US011896449B2

(12) United States Patent
Ebrahimi

(10) Patent No.: US 11,896,449 B2
(45) Date of Patent: Feb. 13, 2024

(54) SNAPON ADJUSTABLE IMPLANT SURGICAL DRILL STOP AND SURGICAL GUIDE

(71) Applicant: Sohail M. Ebrahimi, Redwood City, CA (US)

(72) Inventor: Sohail M. Ebrahimi, Redwood City, CA (US)

( * ) Notice: Subject to any disclaimer, the term of this patent is extended or adjusted under 35 U.S.C. 154(b) by 0 days.

(21) Appl. No.: 15/356,550

(22) Filed: Nov. 19, 2016

(65) Prior Publication Data

US 2018/0140378 A1 May 24, 2018

(51) Int. Cl.
| *A61C 1/08* | (2006.01) |
| *A61C 1/06* | (2006.01) |
| *A61C 1/05* | (2006.01) |
| *A61C 5/44* | (2017.01) |
| *A61B 1/07* | (2006.01) |
| *A61B 1/24* | (2006.01) |
| *A61C 1/00* | (2006.01) |
| *A61C 3/02* | (2006.01) |
| *A61B 90/00* | (2016.01) |

(52) U.S. Cl.
CPC ............... *A61C 1/082* (2013.01); *A61B 1/07* (2013.01); *A61B 1/24* (2013.01); *A61C 1/0061* (2013.01); *A61C 1/05* (2013.01); *A61C 1/06* (2013.01); *A61C 1/084* (2013.01); *A61C 1/088* (2013.01); *A61C 3/02* (2013.01); *A61C 5/44* (2017.02); *A61B 2090/034* (2016.02); *A61B 2090/036* (2016.02); *A61C 2201/002* (2013.01)

(58) Field of Classification Search
CPC ......... A61C 1/082; A61C 1/0061; A61C 1/05; A61C 1/06; A61C 1/084; A61C 1/088; A61C 5/44; A61C 3/02; A61C 17/02; A61C 2201/002; A61B 1/07; A61B 1/24; A61B 2090/034; A61B 2090/036; B23B 49/003; B23B 49/006; B23B 49/008
USPC .................. 433/72–76; 606/80, 96; 269/3, 6
See application file for complete search history.

(56) References Cited

U.S. PATENT DOCUMENTS

| 2,924,013 | A | * | 2/1960 | Wowra ...................... A61C 1/16 |
| | | | | 433/116 |
| 3,590,232 | A | * | 6/1971 | Sadowski ................ A61B 1/07 |
| | | | | 362/119 |
| 5,876,204 | A | * | 3/1999 | Day ........................ A61C 1/084 |
| | | | | 433/173 |
| 2010/0173259 | A1 | * | 7/2010 | Vogel ..................... A61C 1/084 |
| | | | | 433/72 |

FOREIGN PATENT DOCUMENTS

WO    WO-2010010029 A1 *  1/2010  ........... A61C 1/0015

* cited by examiner

*Primary Examiner* — Cris L. Rodriguez
*Assistant Examiner* — Drew S Folgmann
(74) *Attorney, Agent, or Firm* — Walt Froloff

(57) ABSTRACT

A snap-on snap-off drill stop device for boring into a tooth and or in bone. The stop device that impedes insertion of the bore device into the tooth or bone tissue beyond predetermined depths at pre-selected stages of a drilling process by simplifying the tedious process of exchanging drill bits and drill stops for the ultimate size and depth bore.

7 Claims, 9 Drawing Sheets

Prior Art - Drill Stop with drill guide

SNAPON ADJUSTABLE IMPLANT SURGICAL DRILL STOP AND SURGICAL GUIDE

BACKGROUND

Field of the Invention

The present invention relates to devices for surgical drilling a bore in a tooth and or in bone and, in particular to a stop device that enforces a metered insertion of the bore device into the tooth or bone tissue to predetermined depths with a guide at stages of a surgical drilling process.

The standard teaching of surgical dental implant drilling process typically begins with drilling a small hole to a depth and diameter using a specific drill and drill stop of the appropriate length and size to prevent drilling beyond a specific depth. Thus for drilling a socket to a predetermined depth and diameter which is sized to receive an implant includes a first pilot drill bur with a first bur diameter, a second drill bur with a second bur diameter, wherein the second bur diameter is greater than the first bur diameter. A stop collar is provided which includes a body with a first bore formed through the body. The first bore is adapted to receive the first drill bur. A second bore is formed coaxial with the first bore and extends a portion less than an entire length of the body, wherein the second bore is greater than the first bore and adapted to receive the second drill bur.

Typically the drill bit will have a shaft and a drill-bit body, the drill-bit body having a point at an operative end, the drill-bit body further having a mark at a predetermined distance from the point to demark the drilling depth distance. This functions in conjunction with a drill stop of some kind. Typically a drill stop will have a collar, manually placed for each drill bit, and generally oriented such that a longitudinal axis of the stop-collar body is substantially normal to a drilling site on a patient, such that the second end of the stop-collar body is closer than the first end of the stop-collar body to the drilling site, an axial bore extending through the stop-collar body, wherein the axial bore extends the entire axial body length from the first end of the stop-collar body to the second end of the stop-collar body, coaxial with the longitudinal axis of the stop-collar body, wherein the axial bore has an axial-bore diameter, wherein the stop collar comprises securing means for securing the first drill bit in the axial bore such that the drill-bit body of the first drill bit extends the predetermined distance beyond the second end of the stop-collar body when the first drill bit is secured by the securing means such that the mark on the drill-bit body of the first drill bit is aligned with the second end of the stop-collar body. Thus the intricacy of the small but precision vital components require a substantial effort in exchanging the drill bits and drill stops along a prescribed chain of progressive drill diameters and stop sizes necessary.

The drilling hole is then expanded step wise, bore with counter-bore, changing to a larger diameter drill bit and a drill bit size accommodating drill stop for the next stage diameter drill bit, again manually and with what seems eternity as the patient sits with much apprehension awaiting the next drilling. Replacing the drill bit and also the drill stop are not insignificant steps, as drill bits and drill stops are relatively small components that require precision installing and securing. An poorly designed or secured drill bit or drill stop is as harmful as the wrongly installed-secured drill bit and/or drill stop. However by the processes discrete nature, steps are repeated many times to expand the drill hole to the desired hole step size and depth. This process can become problematic as changing drill bits and associated drill bit stops must progress in a definite pattern and order. Any misplacement or out-of-order exchange can have drastic consequences and potentially irreversible nerve damage. Safety concerns dominate designs such that designs and process become brutally complex.

Another aspect of surgical drilling for dental implants includes the creation of dental drill guides, which are special and unique plastic and metal molds created to conform with a patient's mouth inside features. These molds are formed to mark the drill site and guide the surgeon in drilling in the correct locations and to minimize site offset error. Currently the guides work together with sets of drill stops to prevent any deeper drilling penetration. These dental guides are patient unique and are hance expensive to make and significantly add to the patients cost of dental health care.

What is needed are methods and mechanisms to reduce the surgeon's or dentist's mental and physical logistics for exchange of drill bits and stop collar components during the drilling process. What is needed are dental surgery devices and methods that do not further compromise the safety of the patient from damaging drilling through complex procedures fraught with potential for error where is near zero tolerance. What are needed are more efficient ways to effect the step wise surgery with the drill and stops. What is needed are ways to shorten the surgery time without compromising client safety. Also what is needed are ways to aid surgeons in drilling without expense adding patient unique drill guides and without compromising patient safety.

SUMMARY

The present invention discloses a snap-on adjustable dental surgical drilling stop device having a snap-on drill stop having two ends, the first end conforming with to a hand piece drill handle with snap-on drill stop end surface contact from the snap-on drill stop to the drill side of the hand piece and partially extending around the hand piece for rigidly snap-coupling the drill stop with the hand piece, the snap-on drill stop having a midsection elbow forming from the snap-on component into a collar element with center disposed co-axial to a drill bit and conformably fitting to the drill assembly drill bit protruding end, and the snap-on drill stop second end having a drill bit parallel neck extending from the elbow midsection forming collar element to a length short of the drill bit distal end providing an impediment to any drill bit progress into a drill bit normal surface, whereby the snap-on drill stop can be inserted and/or removed manually without removing the drill bit and where the drill depth is quickly ascertainable.

The snap-on adjustable dental implant surgical drilling stop device can have color coded snap-on stops and various length and size stop snap-on surface.

BRIEF DESCRIPTION OF DRAWINGS

Specific embodiments of the invention will be described in detail with reference to the following figures.

DETAILED DESCRIPTION

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

OBJECTS AND ADVANTAGES

An object of the inventions is to provide a safe method of controlling the depth of the drill bit to avoid reaching a patient's nerve while drilling into tooth or bone and for protection of the sinus cavity.

Another object is of this invention is to simplify the drilling process and method by having a drill stop that can remain on the drilling device as the drill bits are exchanged.

Still another object of the invention is to provide safer ways of exchanging drill bits without mistaking and misplacing accommodating drill stops using markings demarking size ranges which are large and easily visually ascertained.

Another object of the invention is to provide dental surgery devices and methods that do not further compromise the safety of the patient from damaging drilling through complex procedures fraught with potential for error where is near zero tolerance.

Yet another object of the invention is to provide more efficient ways to effect the step wise surgery with the drill bits and stops and to shorten the surgery time without compromising client safety.

Another object of the invention is complication prevention from maxillary sinus perforations and inferior alveolar nerve damage, or metal frame and nerve damage.

Another object of the invention to provide simple methods for the surgeon to ascertain the drill bit depth of insertion from the stop to the drill bit distal end before drilling.

Yet another object of the invention is to provide a built-in guide for the drill so that a surgeon need not buy extra surgical guide drils for guided surgery. They can use their regular drills for ostotomy.

Another object of the invention is to provide for smartly attaching-detaching irrigation ducts and optical fiber directed at a drilling site.

Yet another object of the invention is to reduce surgeon stress and procedure time in practice.

DRAWING DETAIL DESCRIPTION

Figure 1:
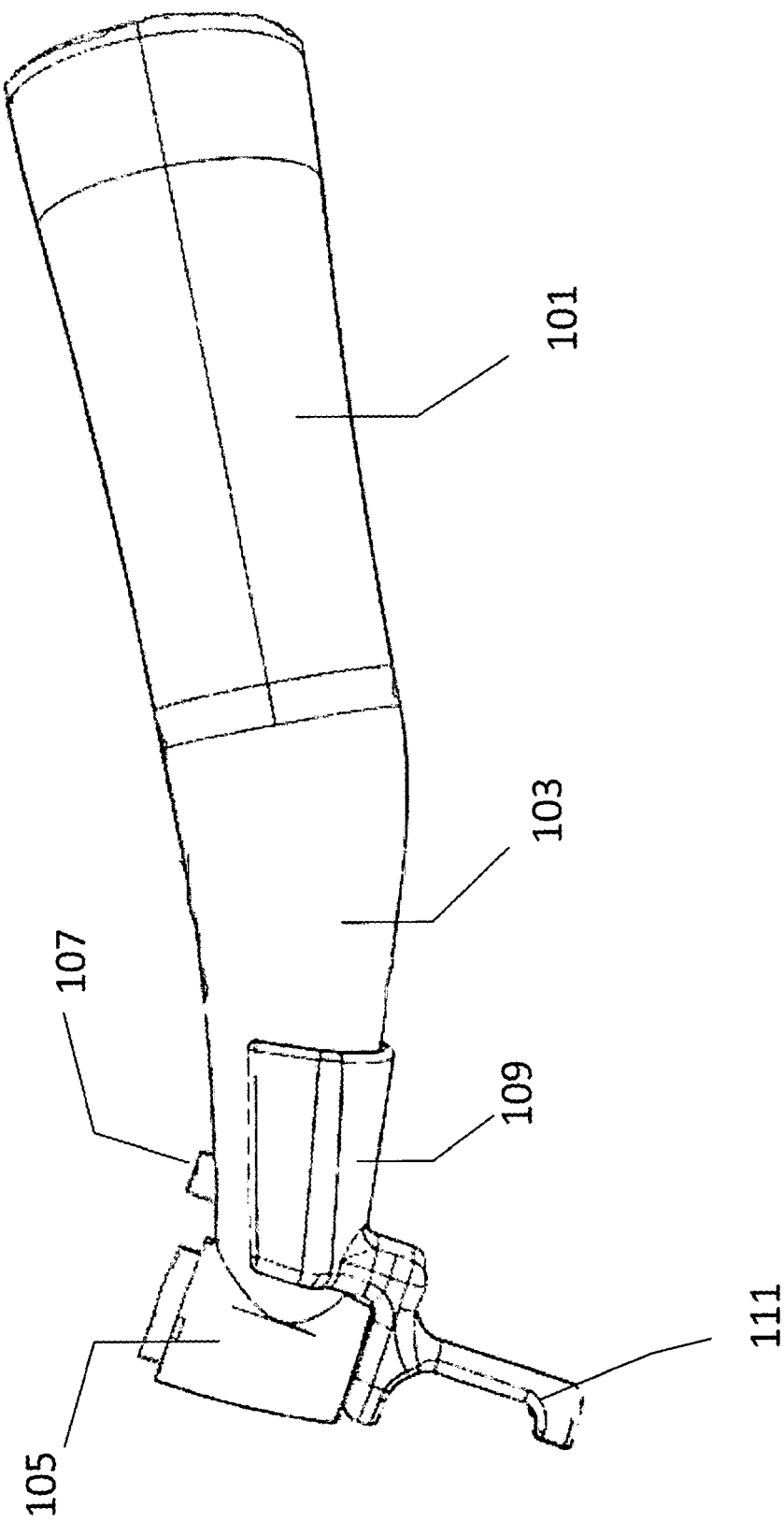
FIG. 1 shows an adjustable snap-on drill stop snap coupled a typical surgical dental drill in accordance with an embodiment of the present invention.

FIG. 1 shows an adjustable snap-on drill stop snap coupled a typical surgical dental drill in accordance with an embodiment of the present invention.

The stop snap 109 on fits on a drill handpiece having two ends, a hand grip end 101 and drill assembly attachment end 103. The hand grip end 101 will generally have power input for air or electric motor drive mechanism, motor drive mechanism having the typical drill drive components in the handpiece including locking catch, drive coupling, drive shaft, gear box shaft coupling to drill bearing assembly for transferring mechanical power to the drill assembly end 103. The drill assembly end 103 has a transversely coupled drill housing 105 comprising a drill drive assembly mechanically coupled to the hand piece motor or turbine drive. The drill drive assembly 105 is coupled to an exchangeably insertable drill bit, which will be exchanged several times in each operation generally depending on the surgeon's assessment of the degree of vertical and horizontal bone placement capacity that exists, number of drill bit exchanges needed.

In one embodiment the drill stops 111 are removable and interchangeable by simply snapping 109 then on the drilling device handle 103, many of which have a tapered body handle 103 portion. Thus a taped snap-on stop 109 conforms with varying degrees of taper to accommodate different dimension of taper handle tools, giving interchangability across dental tools as well as drill stops. In another embodiment of the invention that drill stop can be made as part of the handle of the drill handle-turbine with power from a cord attached to the handle.

Figure 2:
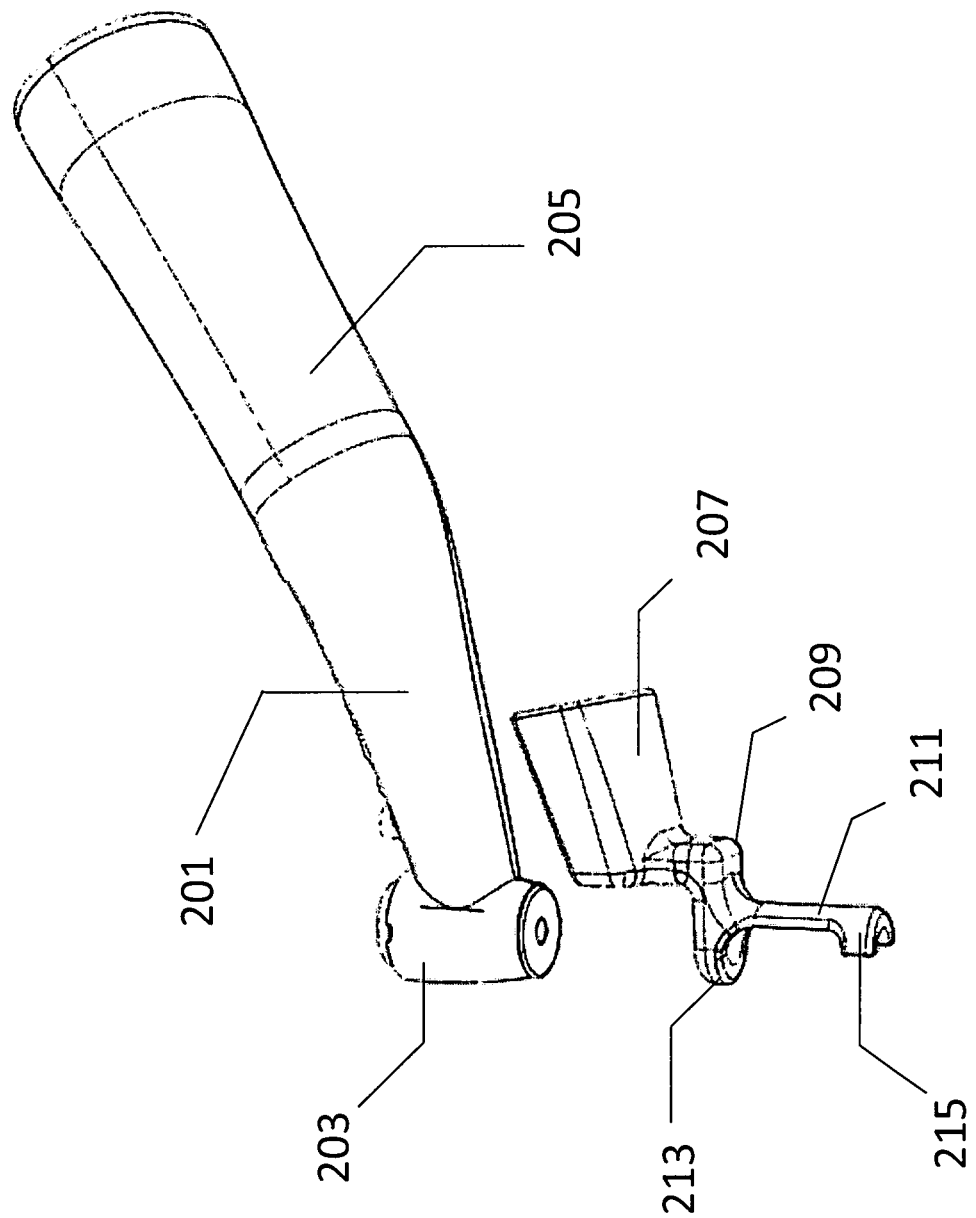
FIG. 2 illustrates an adjustable snap-on drill stop snap assembly with a typical surgical dental drill exterior in accordance with an embodiment of the present invention.

FIG. 2 illustrates an adjustable snap-on drill stop snap assembly with a typical surgical dental drill exterior in accordance with an embodiment of the present invention.

A typical dental implant handpiece 205 may taper into a smaller neck 201 coupled to a drill housing 203. In an embodiment the snap on drill stop shown detached has a snap-on conforming surface 207 end which partially wraps around the drill tool neck 201. The implant handpiece snap-on stop contains an extension 209 from the snap-on surface element 207 to an elbow bending 209 contiguously into a collar element 213 normal to and coaxial with the dental implant handpiece housing 203 centerline. The stop distal end has cuff-like open element 215 which acts as a butt against a drilling surface extends by a snap-stop neck 211 element which extends parallel to the implant handpiece housing 203 centerline. In an aspect of the invention the flat collar element 213 and the open cuff-like distal end element 215 provide the drill bit to be unloaded from the dental implant handpiece housing 203 without disturbing a drill stop and yet provide for the handpiece stop be removed and exchanged without disturbing an installed drill bur.

The snap on conforming surface element 207 may extend along the dental implant handpiece taper 201 portion and or handle 205 to accommodate any handle size dental tool. In an embodiment the snap-stop is color coated and neck 211 clearly marked with the depth marked on each drill side.

Figure 3:
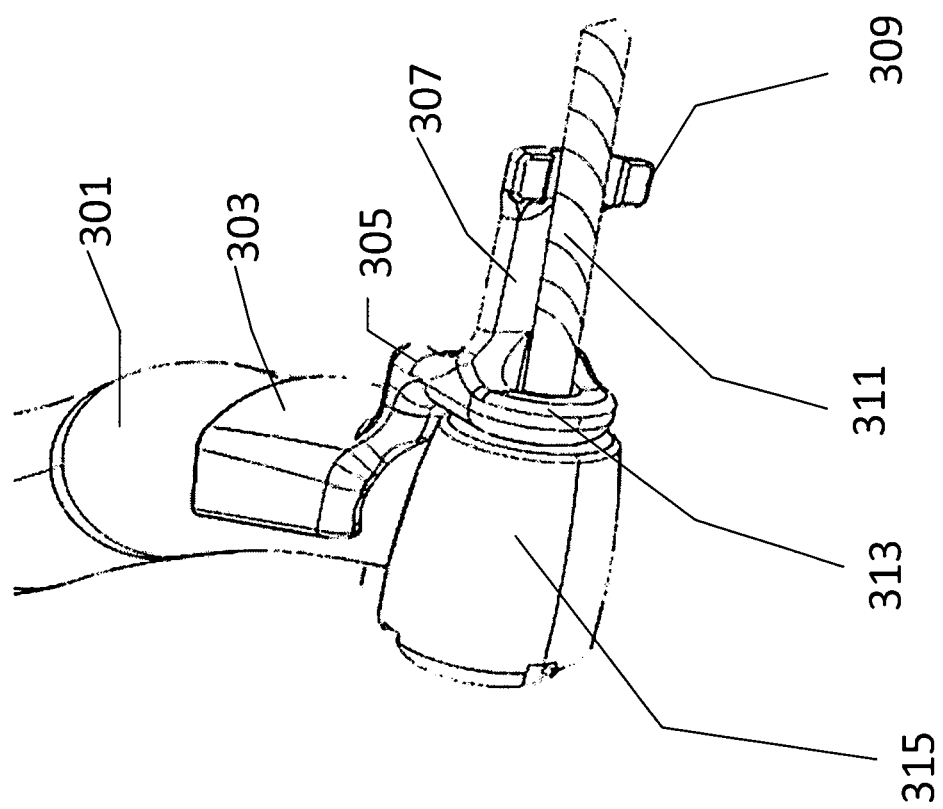
FIG. 3 illustrates an adjustable snap-on drill stop with installed drill bit in a typical surgical dental implant hand-piece drill exterior in accordance with an embodiment of the present invention.

FIG. 3 illustrates an adjustable snap-on drill stop with installed drill bit in a typical surgical dental drill exterior in accordance with an embodiment of the present invention.

In an embodiment of the invention for a typical surgical-dental drill handle bend 301 is coupled to drill motor housing 315 shown at roughly a right angle but can be more or less angular at handle 301 motor housing 315 coupling. An embodiment snap-on drill stop has two ends, the first end is a partial cuff-like surface component 303 conforming and snap coupled to the drill handle 301 surface adjacent to the drill motor housing 315 on the drill bit side. The snap-on drill stop midsection has an elbow or bend 305 with a contiguous collar 313 or washer-like fitting snug against the motor housing 315 and coaxial with an installed drill bit 311, the elbow component extending into a neck extending parallel to drill axis and ending in a partial and open drill collar 309 coaxial with the drill bit 311 centerline. The snap stop distal end 309 partial collar abuts a drilling surface upon contact to impede drilling for a drill bit length extending past the partial collar end 309. The end stop partial collar 309 can also be a closed collar as show with the drill bit collar 313. Thus the end stop collar in some embodiments will take the place of a guild hole for placement and centering of a drill site.

The arcuate radius contiguous collar 313 and stop distal end 309 collar-stop accommodate the largest diameter drill bit such that the progression of drill bits in the drilling process do not require an alternate drill stop for each drill bit. Thus the surgery process does not require the change of drill stop with each new drill bit, reducing the chance of error in drilling too deep and causing injury to tooth, bone or even nerve. In an embodiment of the invention the stop distal end 309 will have an inside radius or outside radius that abuts snuggly with a drill guide sleeve, outside or inside the sleeve guide respectively, hence rigidly supporting the drill in a precisely measured drill position while drilling.

Figure 4:
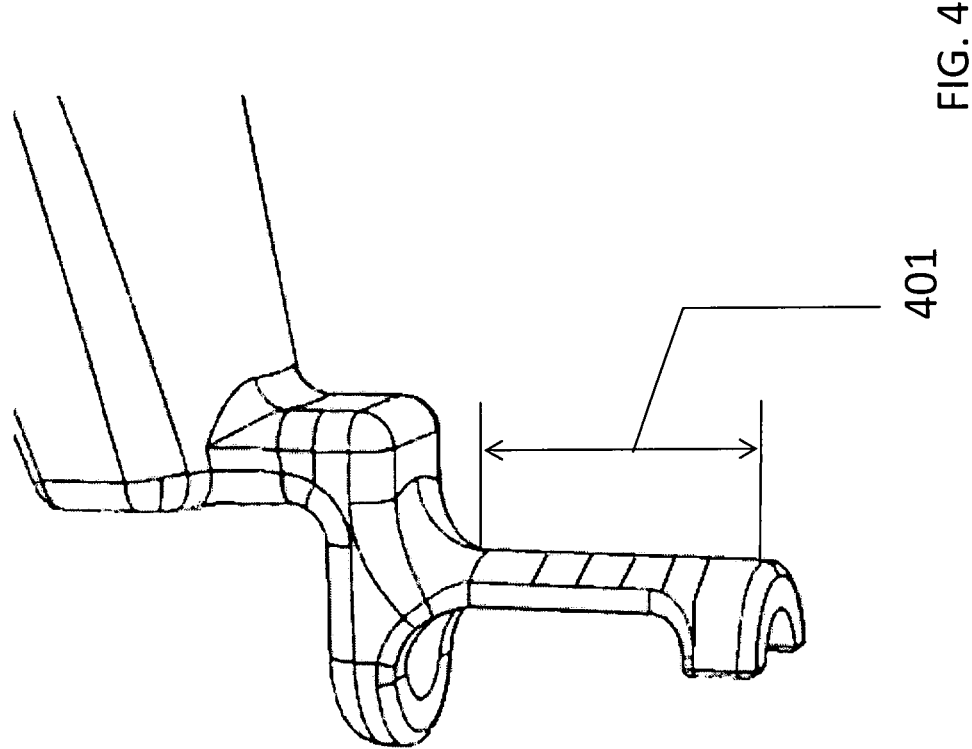
FIG. 4 shows an adjustable snap-on drill stop with drill stop neck 401 marked with a scale according to an embodiment of the present invention.

FIG. 4 shows an adjustable snap-on drill stop with drill stop neck 401 marked with a scale according to an embodiment of the present invention. The scale may be in any dimension and preferably as most easily understood by the drill user.

Figure 5:
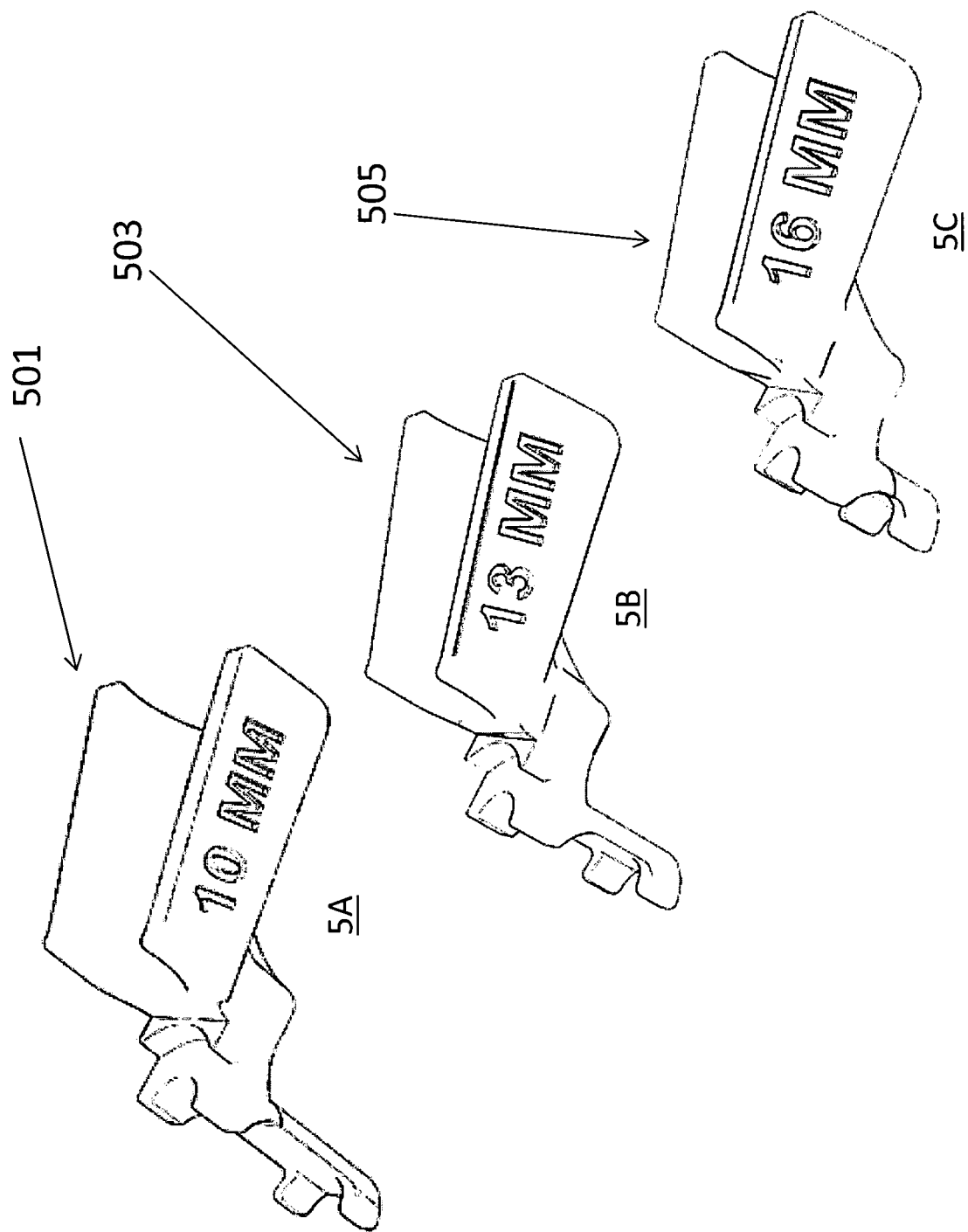
FIG. 5 shows an adjustable snap-on drill stop with drill stop marked on the drill stop snap component according to an embodiment of the present invention.

FIG. 5 shows an adjustable snap-on drill stop with drill stop 501 503 505 marked on the drill stop snap component according to an embodiment of the present invention.

Figure 6:
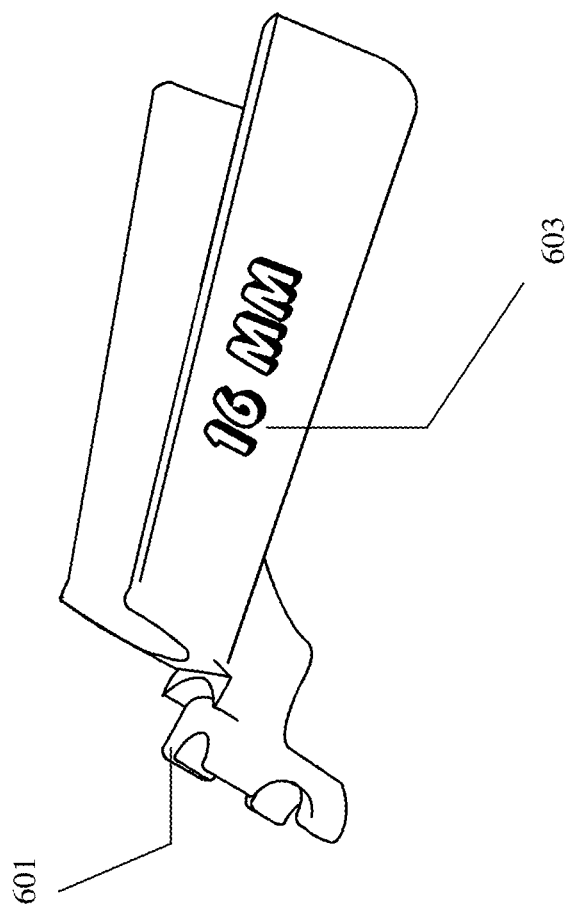
FIG. 6 shows an adjustable snap-on drill stop with stop midsection contiguous formed arcuant but not completely closed collar according to an embodiment of the present invention.

FIG. 6 shows an adjustable snap-on drill stop with drill stop letter marking 603 the stop length on the drill stop snap component and the stop midsection contiguous formed arcuant and concentric to the drill bit centerline with partially open collar 601 according to an embodiment of the present invention. The letter markings 603 or the stop may be color coded for easier visual confirmation and drill bit co-ordination.

Figure 7:
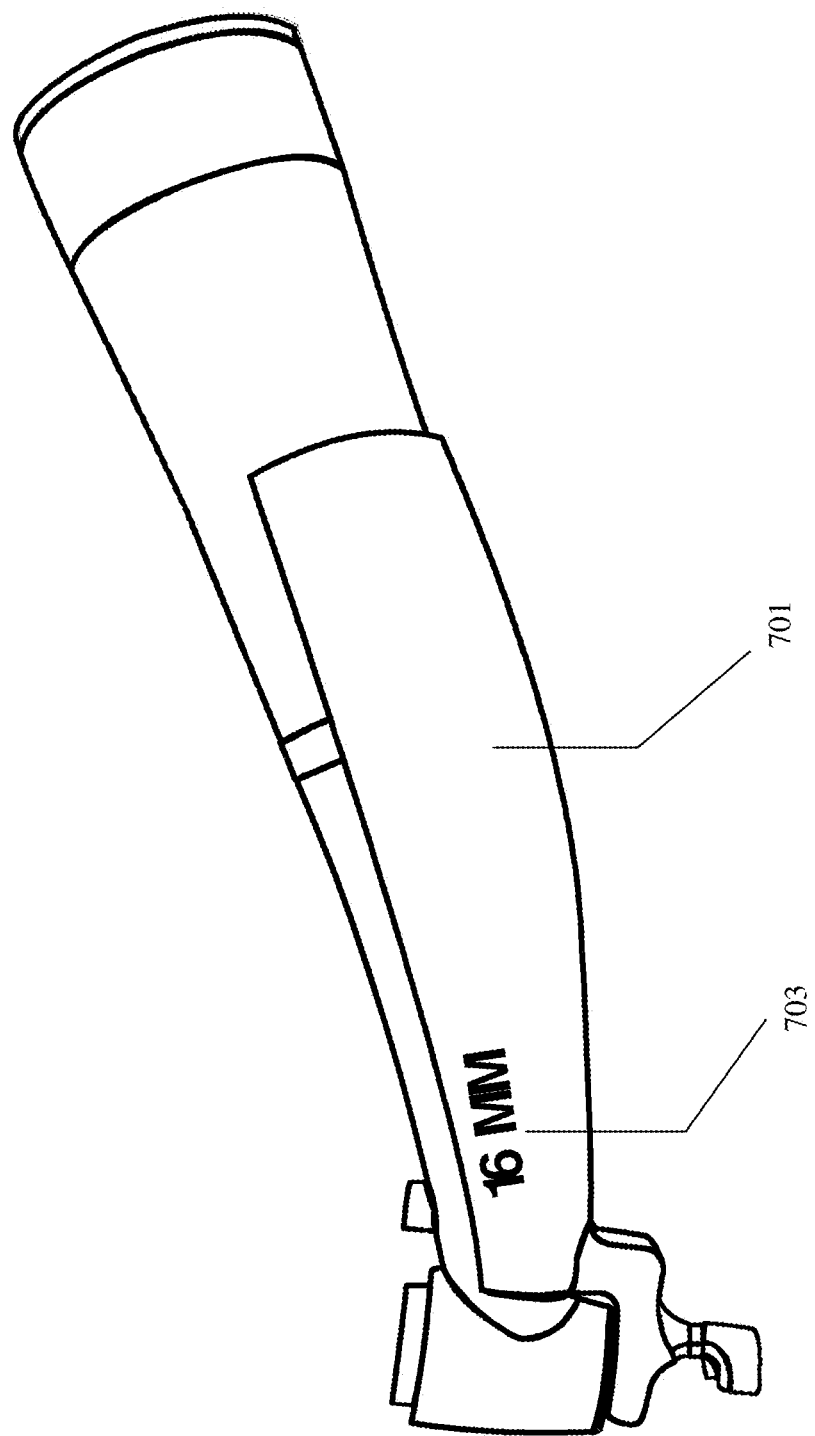
FIG. 7 shows an adjustable snap-on drill stop with drill stop letter marking the stop length on the drill stop snap component extending to near full handle length according to an embodiment of the present invention.

FIG. 7 shows an adjustable snap-on drill stop with drill stop letter marking the stop length 703 on the drill stop snap component extending to near full handle length 701 according to an embodiment of the present invention. The longer snap length provides more snap surface adhesion, additional printable surface which can provide for additional reminders or information, and forms a larger grip on the drill handle for ease of use. In another embodiment the drill stop snap component can be permanently affixed to the drill handle.

Figure 8B:
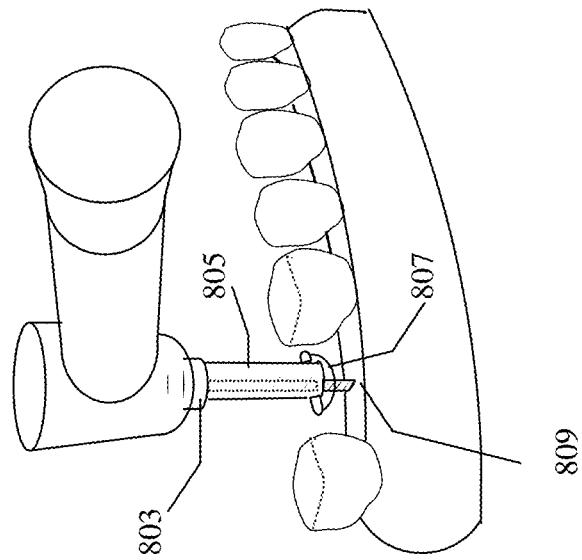
FIG. 8b is an illustration of an adjustable snap-on drill stop and guide in an embodiment of the invention.
Figure 8A:
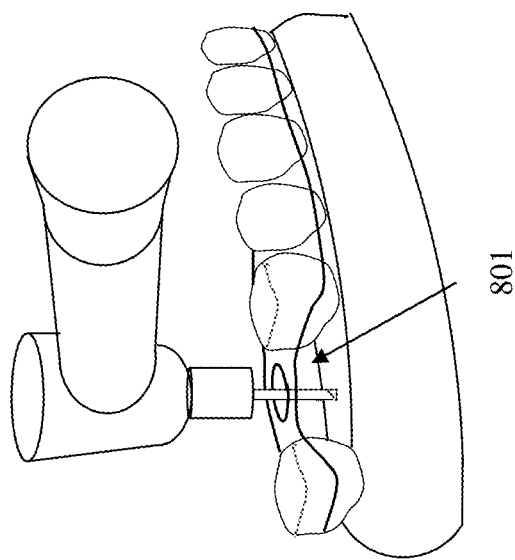
FIG. 8a is Prior Art illustration of independent drill stop in conjunction with a patient unique implant surgical guide.

FIG. 8a is Prior Art illustration of drill with independent drill stop in conjunction with a patient unique drill guide.

FIG. 8b is an illustration of an adjustable snap-on drill stop and guide on the same device in an embodiment of the invention. The snap-on drill stop collar 803 is coupled to the stop neck 805 having the stop and guide lip 807 at the stop distal end showing a protruding drill bit 809 for allowing a metered depth bore. The stop neck 805 component allows the surgeon to physically as well as visually guide the drilling.

Figure 9:
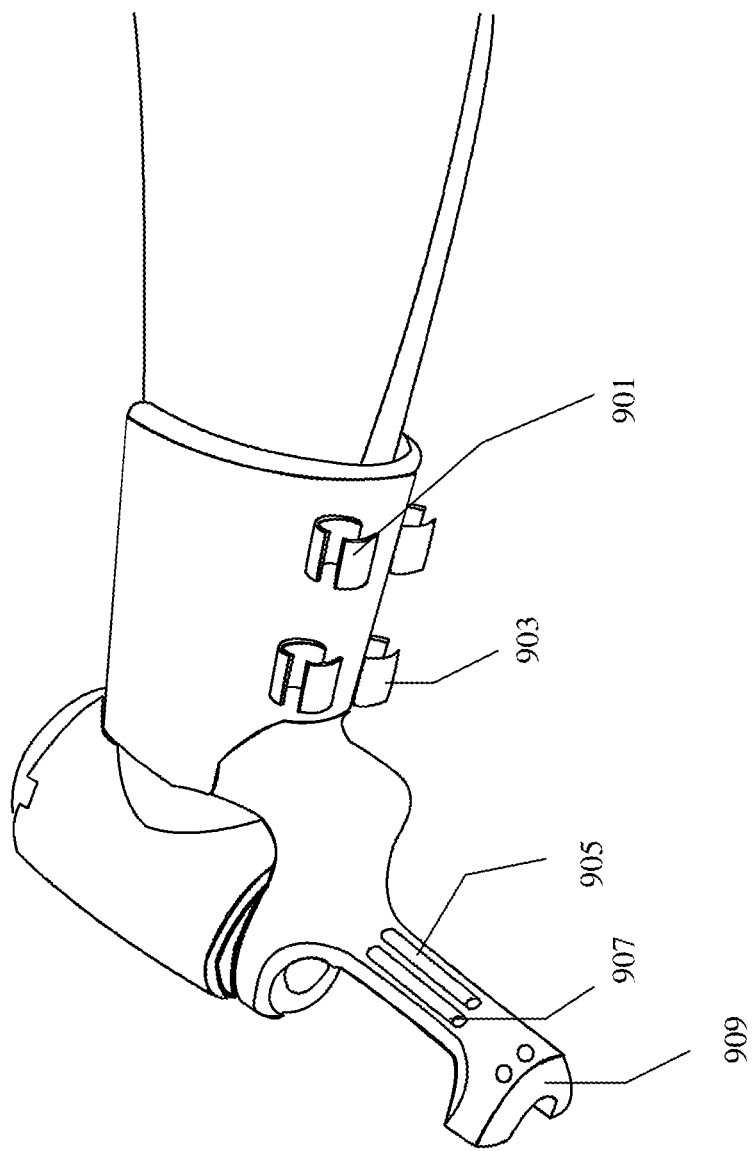
FIG. 9 shows an adjustable snap-on drill stop with drill stop snap component having adjunct snap or clip-on attachments for clip inserting or removing irrigation ducts or optical fiber according to an embodiment of the invention.

FIG. 9 shows an adjustable snap-on drill stop with drill stop snap component and having adjunct snap clip-on components 901 903 clipping on or attaching-detaching irrigation ducts 905, light optical fiber or camera optical fiber 907 from the drill stop snap end to the drill stop distal end for providing fluid or light to the drill site.

The snap-on adjustable dental implant drilling stop and surgical guide also provide a way for a surgeon to use the invention stop with the surgeon's regular dental implant drills. This is a substantial cost savings as the surgeon need not obtain an alternate set of surgical guide drills. Moreover the device provides a stop comparable to most surgical guides, also surgical stents. Thus an aspect of the invention can snap-on stop dimensionally accommodates a surgeon's regular dental implant drills.

Therefore, while the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

What is claimed is:

1. A single-piece snap-on interchangeable dental surgical drill stop device comprising:
    a single-piece snap-on drill stop having two ends, a first end adapted to taper fit to a hand grip drill handle, the first end partially adapted to the hand grip for rigidly snap-coupling the drill stop device with the hand grip drill handle;
    the snap-on drill stop first end having a midsection elbow bending into and permanently continuous to an open drill stop cuff-like collar element with center disposed co-axial to a drill bit and conformably fitting to a drill assembly drill bit, the collar element extruding and permanently coupled to and protruding into the open drill stop cuff-like collar element at the distal second end, and
    the snap-on drill stop second end having a drill bit parallel neck permanently continuous with the elbow midsection and collar element to a length short of the drill bit distal end with the open drill stop cuff-like collar element providing an impediment to any drill bit progress into a drill bit normal surface,
    whereby the snap-on drill stop device can be inserted and/or removed manually without removing the drill bit and where the drill depth is quickly ascertainable by inspection of the protruding distance below the open drill stop cuff-like collar element.

2. The single-piece snap-on on interchangeable dental surgical drill stop device of claim 1 further comprising color coded snap-on drill stop.

3. The single-piece snap-on on interchangeable dental surgical drill stop device of claim 1 further comprising letter marking displaying snap-on drill stop dimensions.

4. The single-piece snap-on on interchangeable dental surgical drill stop device of claim 1 further comprising color coded snap-on drill stops for drill bit coordination.

5. The single-piece snap-on on interchangeable dental surgical drilling stop device of claim 1 wherein an arcuate radius stop collar and stop distal end accommodate an interchangeable diameter drill bit.

6. The single-piece snap-on on interchangeable dental surgical drilling stop device of claim 1 further comprising a distal end of the open drill stop cuff-like collar element is coupled to a stop neck having a stop and guide lip at the stop distal end for viewing a protruding drill bit to a metered depth bore.

7. The single-piece snap-on on interchangeable dental surgical stop device of claim 1 further comprising snap clip-on components for clipping on or attaching-detaching irrigation ducts, light optical fiber or camera optical fiber from a drill stop snap end to the drill stop distal end for providing fluid or light to the drill site.

* * * * *